(12) United States Patent
Heinonen (10) Patent No.: US 6,530,370 B1
(45) Date of Patent: Mar. 11, 2003

(54) NEBULIZER APPARATUS

(75) Inventor: Erkki Heinonen, Helsinki (FI)

(73) Assignee: Instrumentation Corp., Helsinki (FI)

( * ) Notice: Subject to any disclaimer, the term of this patent is extended or adjusted under 35 U.S.C. 154(b) by 0 days.

(21) Appl. No.: 09/397,529

(22) Filed: Sep. 16, 1999

(51) Int. Cl.[7] .......................... A61M 11/00; B05B 17/06
(52) U.S. Cl. ........................... 128/200.16; 128/200.14; 128/203.12; 239/338
(58) Field of Search .................. 128/200.16, 200.18, 128/200.14, 203.12; 239/102.2, 338, 68

(56) References Cited

U.S. PATENT DOCUMENTS

| | | | |
|---|---|---|---|
| 3,812,854 A | | 5/1974 | Michaels et al. |
| 5,152,456 A | * | 10/1992 | Ross et al. ................ 239/102.2 |
| 5,261,601 A | * | 11/1993 | Ross et al. ................ 239/102.2 |
| 5,443,059 A | | 8/1995 | Koch et al. |
| 5,487,378 A | | 1/1996 | Robertson et al. |
| 5,515,841 A | * | 5/1996 | Robertson et al. ...... 128/200.14 |
| 5,586,550 A | | 12/1996 | Ivri et al. |
| 5,758,637 A | * | 6/1998 | Ivri et al. ................ 128/200.16 |
| 6,076,519 A | * | 6/2000 | Johnson .................. 128/200.14 |
| 6,085,740 A | * | 7/2000 | Ivri et al. ................ 128/200.16 |
| 6,158,431 A | * | 12/2000 | Poole ...................... 128/203.12 |
| 6,192,882 B1 | * | 2/2001 | Gonda ..................... 128/203.21 |
| 6,196,219 B1 | * | 3/2001 | Hess et al. ............... 128/200.21 |

FOREIGN PATENT DOCUMENTS

| | | |
|---|---|---|
| DE | 37 10 141 | 10/1988 |
| EP | 798007 | 10/1997 |
| GB | 2099710 | 12/1982 |
| GB | 2272389 | 5/1994 |
| WO | 92/11050 | 7/1992 |

* cited by examiner

*Primary Examiner*—Aaron J. Lewis
*Assistant Examiner*—Darwin P. Erezo
(74) *Attorney, Agent, or Firm*—Andrus, Sceales, Starke & Sawall, LLP (57) ABSTRACT

A nebulizer apparatus to atomize liquid solutions or suspensions. The nebulizer is typically used in conjunction with a breathing circuit to deliver atomized medicine to a patient. A housing with an opening covered by a thin mesh plate is supplied with the liquid to be nebulized on an "on-demand" basis. The mesh plate or liquid is vibrated at ultrasonic frequencies to atomize the liquid as it passes through the plate into breathing gases flowing through the breathing tube.

29 Claims, 7 Drawing Sheets

NEBULIZER APPARATUS

BACKGROUND OF THE INVENTION

The present invention relates to an improved nebulizer apparatus. Nebulizers, or atomizers, are devices, which generate a fine spray or aerosol, usually of liquid. A particularly useful application for nebulizers is to provide a fine spray containing a dissolved or a suspended particulate or colloidal pharmaceutical agent for administration to a subject by inhalation. Such inhalation treatment is highly effective for conditions affecting the subject's respiratory organs. Further, since the lungs are close to the heart and the blood circulatory system of the body, drug administration by inhalation provides an effective and rapid delivery system to all organs of the body.

In many cases, the nebulizer is placed directly in the mouth or nose of the subject so that the spray can be entrained in the respiratory gases inhaled during normal, spontaneous breathing of the subject. In other cases, the subject breathes with the aid of a respiratory ventilator. A typical ventilator has a breathing circuit comprising an inhalation limb and an exhalation limb connected to two arms of a Y-connector. The third arm of the Y-connector is connected, via a patient limb, to a mouthpiece, mask or endotracheal tube for the subject. The ventilator provides a complete or partial supply of respiratory gases to the subject through the inhalation limb during inhalation. The contraction of the subject's lungs discharges gas through the exhalation limb during exhalation. When a nebulizer is employed in conjunction with a ventilator, it is typically placed in the patient limb.

Nebulizers currently in use for ventilator applications generate the spray either pneumatically or by means of ultrasonic vibrations. Pneumatic nebulizers are typically used with a liquid, such as an aqueous drug solution. High pressure driving gas is conducted through a nozzle to draw the drug from a drug supply for the nebulizer. The drug is discharged against a baffle or other means in a gas space of the nebulizer, breaking the liquid into a fine spray. The gas space is in fluid communication with the inhaled gas pathway of the breathing circuit so that the gas flow expelled from the nozzle along with the nebulized drug is conducted to the breathing circuit and ultimately to the subject.

Disadvantages in the use of pneumatic nebulizers include the following. If the nebulizer adds a significant quantity of gas, for example, up to five liters/minute, into the breathing circuit, the breathing gas composition is affected. The driving gas is most often either oxygen or air and, particularly when a ventilator is used in the treatment of a child, the gas flow from the nebulizer may form a major portion of the inhalation gas flow. Because of the gas flow from the nebulizer, control over the inhalation gas composition is lost. Also, due to passage of the driving gas through the nozzle, impingement of the drug on the baffle, etc., pneumatic nebulizers are noisy. This may contribute to the discomfort of the subject. And, as controlling the commencing and stopping of a drug agent spray is difficult and is not very accurate, pneumatic nebulizers are commonly active during both inhalation and exhalation. This obviously decreases the efficiency of drug delivery as measured by ratio of the amount of drug supplied to the nebulizer and the amount of drug actually delivered into the subject's air ways.

In an ultrasonic nebulizer, the fine spray is produced by ultrasonic vibration of the liquid, as by a piezoelectric crystal. The liquid is dropped on, or otherwise applied to, the crystal. The on-off operation of such nebulizers is easier to control than for a pneumatic nebulizer. However, prior art ultrasonic devices require a large electrical power consumption to power the crystal and may not be able to nebulize colloidal or particulate suspensions. Partly due to the high power consumption of ultrasonic nebulizers, the equipment tends to be bulky. This can cause considerable difficulties, given the crowded environment that may surround a subject, such as a critical care patient.

U.S. Pat. No. 5,443,059, shows an attempt to solve the problem of bulkiness in an ultrasonic nebulizer. In the '059 patent, a liquid source and metering component are provided in separate control unit that can be located at a distance from the subject. The control unit meters liquid through a feed line to a piezoelectric ceramic plate positioned in the patient limb of the breathing circuit. The piezoelectric ceramic plate nebulizes the liquid. In the event more liquid is delivered than can be nebulized, the device is equipped with a collection vessel for the excess liquid. In the structure disclosed in this patent, the metering line for the liquid to be nebulized is located above the vibrating crystal so that the liquid drops onto the crystal. However, this renders the ultrasonic nebulizer of this patent position sensitive. Additionally, during inhalation, the flow speed of the respiratory gases can exceed 10 m/s. Such a flow speed can draw the droplets of liquid away into the respiratory gases without the droplets being applied to the vibrating crystal for nebulization. This may render the inhalation therapy less effective, or may alter dosage rates, both of which can adversely affect the subject.

U.S. Pat. No. 3,812,854 describes a nebulizer for inhalation therapy in which the spray is generated on the front surface of a vibrating, porous body. The pores of the body form a network of passages that enable the liquid to flow through the body. The liquid to be nebulized is supplied under pressure from a liquid supply through a liquid conduit to the pores, and forced through the pores to the front surface of the porous body where it is discharged as a spray.

However, the complicated flow paths in the porous body increase the flow resistance so that high liquid pressure is required to transport the liquid through the body. To resist the forces resulting from the high liquid pressure, a thick porous body is required. But, such thickness increases the weight of the nebulizer as well as the amount of electric power required to vibrate same. Also, when used with suspensions containing suspended particulate or colloidal particles, the particles may be entrapped in the complicated flow paths through the porous body.

U.S. Pat. No. 5,478,378 describes a nebulizer in which the aerosol is formed using a mesh plate instead of a porous solid body, thereby to lessen or eliminate the foregoing shortcomings. The mesh plate has a plurality of orifices for the liquid in a reservoir. The orifices are tapered outwardly toward the outlet for the liquid. The liquid or the nozzle assembly is vibrated ultrasonically by a piezoelectric element to nebulize the liquid. The liquid reservoir is preferably permanently filled with liquid and maintained at a slight negative pressure.

BRIEF SUMMARY OF THE INVENTION

An object of the present invention is to provide an improved nebulizer apparatus of the mesh plate type that can atomize both solutions and suspensions without clogging. Another object of the invention is to provide such an apparatus that has a liquid supply control means and a means for substantially equalizing pressures in the nebulizer apparatus with pressures in the breathing circuit. These means avoid pressure stressing of the mesh plate and avoid leaking of the liquid to be nebulized through the mesh plate. Yet another object of the invention is to provide such an apparatus that has a relative small size and low power consumption thereby facilitating its use. Yet another further object of the invention is to provide such an apparatus that is insensitive to the position in which it is operated. An additional object of the invention is provide such an apparatus that has fast response to activation and deactivation, enabling nebulization to be triggered in response to the subject's breathing pattern. A further object of the invention is to provide such an apparatus that efficiently transforms all the liquid into an aerosol.

Provided in accordance with one aspect of the present invention is a nebulizer apparatus for atomizing a liquid into fine droplets. The aerosol so produced may contain medication to be delivered to breathing gases for a patient. In such an environment, the nebulizer apparatus is mounted in a breathing circuit adapter through which the breathing gases pass. The nebulizer has a housing. A mesh plate spanning a cavity in the housing has one side exposed to the gases passing through the housing. The liquid to be nebulized flows into the cavity from a liquid transport line to a rear surface of the mesh plate. A vibration means vibrates the plate or liquid to cause the liquid to pass through holes in the mesh plate to be broken up into droplets and discharged as an aerosol from the front surface of the mesh plate in the flow of breathing gases. The vibrator means for vibrating the mesh plate or liquid is preferably a piezoelectric element energized by an ultrasonic frequency power service.

The mesh plate employed in the present invention is thin as compared to the ceramic bodies used in prior art nebulizers. This permits reduced operating pressures and forces, less energy to vibrate the plate, and allows the use of suspensions since particulates in a suspension can flow through the paths defined by the holes instead of the myriad of complicated flow paths found in ceramic bodies.

The pressure at the rear surface of the mesh plate and at the front surface of the mesh plate is equalized to avoid stresses in the thin mesh plate. This equalization of pressure is accomplished by the use of a pressure channel in the housing communicating between the cavity in the housing and the breathing gas passage.

The delivery of liquid to be nebulized is preferably controlled responsive to the amount of liquid at the rear surface of the mesh plate. For this purpose, a sensor, such as a pair of electrodes spaced from the rear surface of the mesh plate, may be used for sensing the presence of liquid at the rear surface of the mesh plate by changes in impedance. When the appropriate amount of liquid has been delivered, delivery of liquid is stopped or altered to prevent undue pressure in the volume and resulting stress on the plate or liquid leakage through the mesh plate. The supply of liquid is resumed when the liquid on the mesh plate has been consumed or reduced, as detected by the sensor. In an embodiment of the invention, the mesh plate may serve as one of the electrodes. Or, an optical sensor may be used as a liquid detector.

The nebulizer apparatus may include a control valve connected in a liquid transport line for the liquid to be nebulized. This valve may be opened and closed, responsive to the sensor, to control the liquid flow through the transport line to the mesh plate.

A reservoir for the nebulizer apparatus connected to the liquid transport line stores the liquid prior to nebulization. The reservoir may be pressurized to supply liquid to the liquid transport line. Alternatively, a pump or elevated reservoir may be used to supply the liquid.

If small amounts of liquid are to be delivered, a predetermined amount of the liquid may be stored in a two-part reservoir prior to nebulization. One part of the reservoir comprises a chamber for receiving the liquid to be nebulized. This chamber is separated from the other part of the reservoir by a flexible wall. The other part of the reservoir is pressurized with liquid or gas to supply the liquid from the chamber to the liquid supply line.

To avoid condensation on the front surface of the mesh plate in the moist breathing circuit environment, to reduce liquid viscosity, and/or to provide comfort to the patient, a heater, such as a resistor, may be incorporated in the nebulizer apparatus or liquid transport line.

Various other features, objects, and advantages of the invention will be made apparent from the following detailed description and the drawings.

BRIEF DESCRIPTION OF THE SEVERAL VIEWS OF THE DRAWING

The foregoing objects and advantages, as well as the invention itself, will be more fully understood from the attached drawing and following detailed description.

In the drawings:

FIG. 1 is a general cross sectional view of the nebulizer apparatus of the present invention, the operating environment for the nebulizer apparatus being shown in a generalized schematic form;

FIG. 2 is a cross-sectional side elevational view of the nebulizer apparatus shown generally in FIG. 1;

FIG. 3 shows an cross-sectional side elevation of an alternative embodiment of the nebulizer apparatus;

FIGS. 4 and 5 show alternative embodiments for the control apparatus and liquid supply for the nebulizer apparatus shown in FIG. 1;

FIGS. 6(*a*) through 6(*d*) show schematic views of alternative embodiments of the nebulizer apparatus liquid reservoir;

FIG. 7 shows use of an optical liquid sensor;

FIG. 8*a* is an exploded, partial view showing a further embodiment of the nebulizer apparatus according to the present invention; and FIGS. 8*b* and 8*c* are schematic views showing the operation of the nebulizer apparatus of FIG. 8*a*.

DETAILED DESCRIPTION OF THE INVENTION

Nebulizer apparatus 1 of the present invention is typically used in conjunction with breathing circuit 2, ventilator 4 and control unit 6, as shown in FIG. 1. The nebulizer atomizes liquid solutions or suspensions for delivery to a subject, as for example as a drug treatment for a patient. Breathing circuit 2 includes inhalation limb 8, which is coupled to ventilator 4 at inhalation limb connector 10. Exhalation limb 12 is connected to ventilator 4 at exhalation limb connector 14. Inhalation limb 8 and exhalation limb 12 are connected to two arms of Y-connector 16. A third arm of Y-connector 16 is connected to one end of patient limb 18. The other end of patient limb 18 is directed to a mouthpiece, facemask, or endotracheal tube for the subject.

Ventilator 4 provides all or a portion of the respiratory gases for the subject by providing inhalation gases in inhalation limb 8. The inhalation gases pass through Y-connector 16 and into patient limb 18 for supply to the subject. On exhalation, the respiratory gases pass through patient limb 18, Y-connector 16, and exhalation limb 12 back to ventilator 4.

Figure 1:
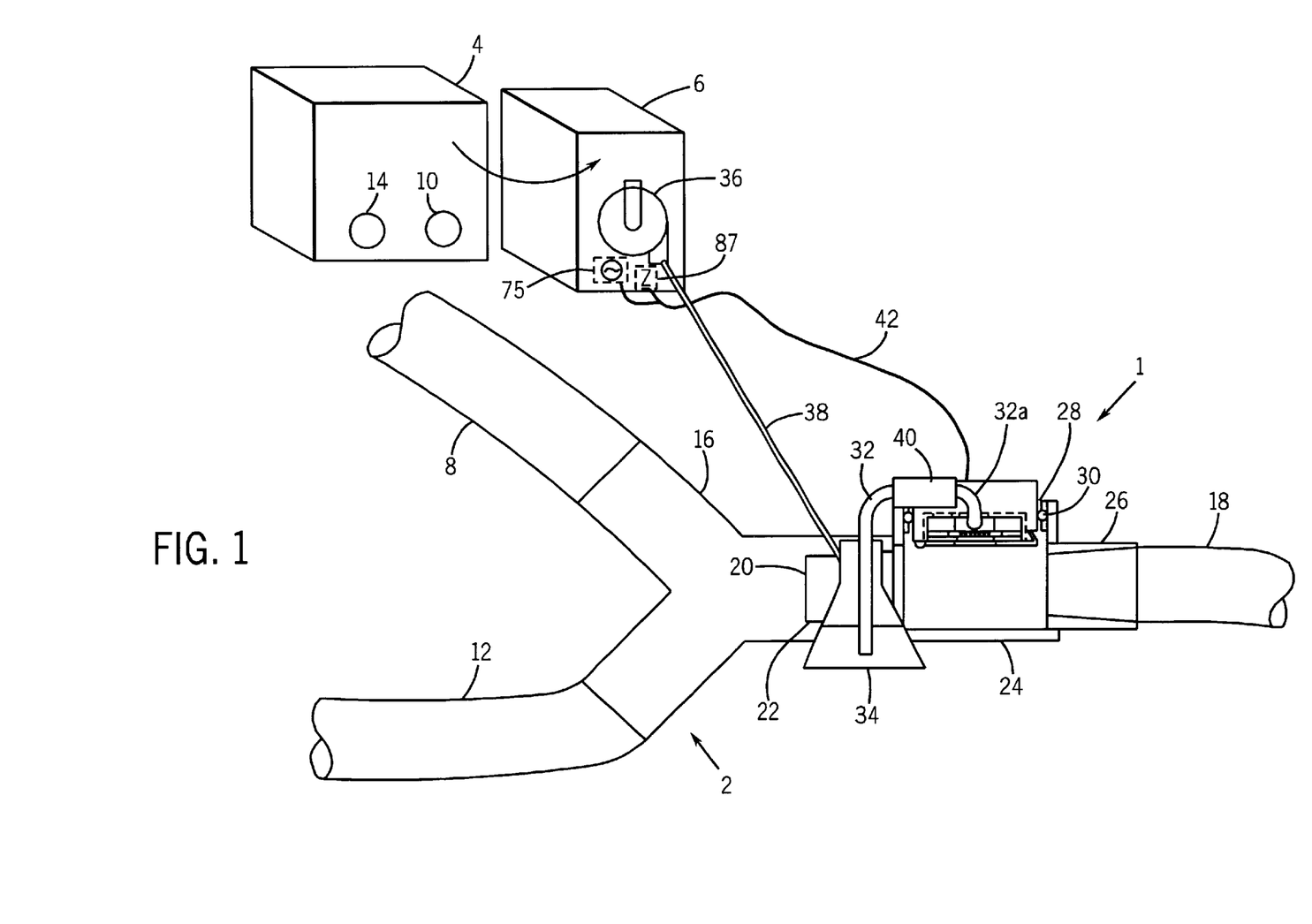

As shown in FIG. 1, nebulizer apparatus 1 is preferably positioned in patient breathing circuit 2 as near the patient as possible to minimize the aerosol transport path, and to minimize the deposition of the aerosol on the breathing circuit walls. To this end, nebulizer apparatus 1 may be inserted in the breathing circuit between Y-connector 16 and patient limb 18. Y-connector 16 has socket 20 for receiving tubular projection 22 of adapter 24 for nebulizer apparatus 1. Tubular socket 26 of adapter 24 receives patient limb 18. The nebulizer apparatus is placed in opening 28 in adapter 24 and held in place with O-ring seal 30. When nebulizer apparatus 1 is not needed, or when the nebulizer apparatus is removed for cleaning or maintenance, a cap (not shown) may be fitted into or over the opening 28 to allow breathing circuit 2 to function in a normal manner. Alternatively, the entire adapter 24 containing nebulizer apparatus 1 may be removed from the breathing circuit and patient limb 18 reconnected to Y-connector 16. Control unit 6 may be located at a distance from nebulizer apparatus 1 and may be incorporated in ventilator 4, if desired.

Nebulizer apparatus 1 is connected to a source of material to be nebulized. In the embodiment shown in FIG. 1, conduit 32 and transport line 32a supply material from reservoir 34 to apparatus 1. Reservoir 34 can be placed at a desired location and can be proximate to, or remote from, nebulizer apparatus 1. Control valve 40 is provided in supply conduit 32 and transport line 32a. Electrical control signals are supplied to control valve 40 via cable 42 from control unit 6. As noted above, the material can comprise an aqueous solution, or a particulate or colloidal suspension, of a pharmaceutical agent. For purposes of explanation, the material undergoing nebulization is hereinafter generally described as a liquid. Reservoir 34 is pressurized by pump 36 in control unit 6. In the embodiment shown in FIG. 1, pump 36 supplies a pressurizing gas to reservoir 34 through pressure line 38.

Figure 2:
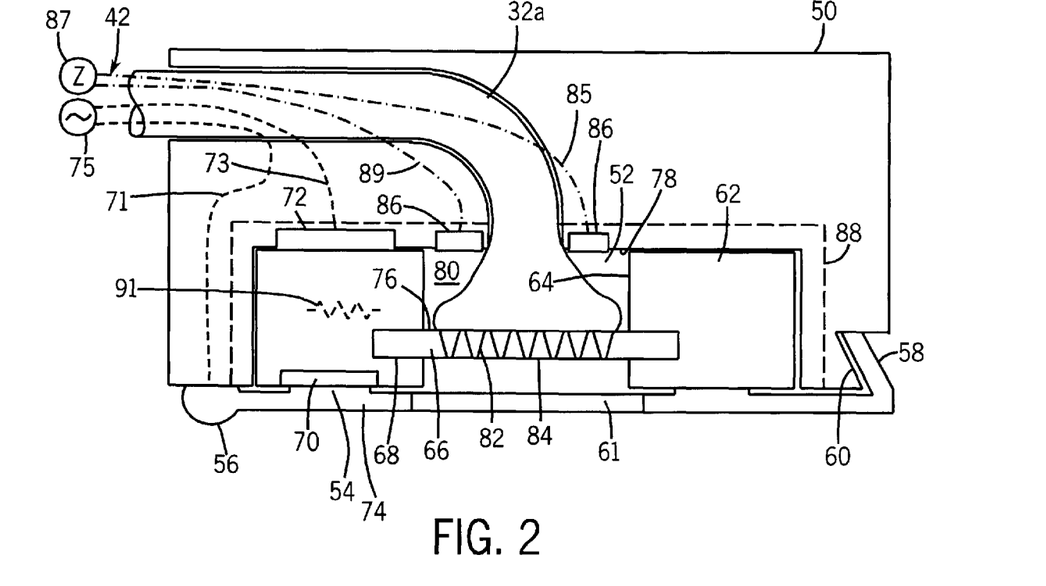

Nebulizer apparatus 1 is shown, in detail, in FIG. 2. The apparatus comprises housing 50 which mounts apparatus 1 in opening 28 of adapter 24 via O-ring seal 30. Housing 50 may be formed of plastic. Housing 50 has a cavity 52. Panel 54 spans cavity 52. Panel 54 is hinged at one edge by hinge 56, and contains a clip 58 at an opposite edge engaging cut-out 60 in housing 50. Panel 54 may be opened by disengaging clip 58 from cut-out 60, to allow the portions of apparatus 1 carrying out the nebulizing of the liquid and positioned in cavity 52 to be removed at the end of therapy for replacement, or for cleaning when a different drug is to be administered to the subject. Panel 54 has an opening 61 in the central portion thereof.

Mesh plate frame 62 is received in cavity 52. Frame 62 may be formed of, for example, aluminum or brass. Mesh plate frame 62 has a centrally located aperture defined by surface 64. Mesh plate 66 spans the aperture with peripheral edge 68 embedded into frame 62 at surface 64. Frame 62 has an ultrasonic vibration generator in the form of piezoelectric element 70 embedded therein to vibrate frame 62, as well as mesh plate 66. Mesh plate frame 62, when placed in cavity 52, contacts terminal 72 in housing 50 and terminal 74 in panel 54. Terminal 72 and 74 are thus connected to piezoelectric element 70. They are also connected, via cable 42 to an electrical power source 75 in control unit 6 having a desired frequency in the ultrasonic range. Typically frequencies range from 50 to 200 kHz. The connections may be carried out by conductors 71 and 73 in frame 62.

Housing 50, frame 62, and mesh plate 66 and cavity 52 may be generally circular in form. When fitted into housing cavity, the rear surface 76 of mesh plate 66, mesh plate frame surface 64 and housing surface 78 define an internal volume 80. Transport line 32a extends through housing 50 to open into volume 80 at surface 78.

Mesh plate 66 is a relatively thin plate having a plurality of holes 82. Mesh plate 12 may be about 0.02 mm thick. The diameter of the holes at front surface 84 is preferably approximately 2–15 $\mu$m in diameter. Such holes may be formed in the plate by an electroforming process, which process produces holes of increasing diameter toward rear surface 76 shown in FIGS. 2 and 3 of the drawing. However, the straight holes, shown in FIGS. 7 and 8 will work equally well, the primary criterion being that the exit diameter in front surface 84 be such as to form droplets of the desired size.

The thinness of mesh plate 66 limits its ability to resist excessive forces generated by liquid pressures in volume 80. Liquid pressure in volume 80 may also cause leaks through holes 82. To insure the proper supply of liquid from transport line 32a, sensing elements, such as a pair of spaced electrodes 86, are fitted in housing 50 to sense the presence or absence of the liquid in volume 80. As shown in FIG. 2, electrodes 86 may be mounted in surface 78 of housing 50 adjacent the outlet of transport line 32a.

Front surface 84 of mesh plate 66 is exposed to the pressure of the breathing gases in breathing circuit 2. These pressures will vary during inhalation and exhalation conditions in breathing circuit 2. For example, with artificial ventilation, breathing circuit pressures may increase up to 100 mbar during inspiration and thereafter decrease during expiration. Housing 50 is provided with pressure balancing channel 88 shown in FIG. 2 that connects volume 80 with breathing circuit 2 for equalizing the prevailing pressure at both sides of mesh plate 66 to avoid pressure stressing mesh plate 66 and causing leaks to occur through the mesh plate.

In operation, valve 40 is opened responsive to a signal from cable 42 and liquid flows through conduit 32 and transport line 32a due to the pressurizing gas in reservoir 34. The liquid flows out the end of transport line 32a into contact with the upper surface of mesh plate 66. The cohesive forces in the liquid form the liquid into a column of liquid extending between the end of transport line 32a and mesh plate 66, generally as shown in FIG. 2. Piezoelectric element 70 is energized from a high frequency source 75 in control 6 through cable 42 and terminals 72 and 74 in housing 50 to vibrate mesh plate 66. The positioning and energization of piezoelectric element 70 may be such as to cause mesh plate 84 to move toward and away from the end of transport line 32a and the liquid being discharged therefrom. The vibrations cause the liquid in volume 80 to pass through holes 82 in mesh plate 66.

At the front surface 84 of the vibrating mesh plate 66, the atomized liquid will grow into drops at each hole 82 due to the liquid surface tension. The drops will increase in size until the expelling forces arising from the movement of mesh plate 66 and the mass of each drop, exceeds the holding force determined by the size of the holes 82 in mesh plate 66, and the surface tension of the liquid. The drops expelled from plate 66 pass through opening 61 in panel 54 into the patient limb 42, and to the subject during inhalation.

To control the transport of liquid from reservoir 34 into the of nebulizing apparatus 1, electrodes 86, positioned in surface 78 of housing 50, detect the presence of liquid between the end of transport line 32a and the rear surface 76 of mesh plate 66 by alteration of the impedance between the electrodes. That is, with the continued supply of liquid, the column will start to bulge and the impedance measured between the electrodes will be significantly altered. A signal from electrodes 86 is inputted to impedance sensor 87 and control unit 6 via conductors 85 and 89 and cable 42 and used to control valve 40 in liquid supply conduit 32 to close the valve. When the impedance changes, due to the liquid receding away from electrodes 86, the control valve 40 opens to again allow flow of liquid from the end of transport line 32a. The supply of liquid in the nebulizer of the present invention may thus be characterized as being of the "on demand" type. The delivery of nebulized liquid can be controlled by continuously vibrating mesh plate 66 and regulating the liquid transport control or by regulating the activation of mesh plate vibration and intermittently supplying liquid when the amount of liquid in volume 80 is reduced.

Figure 7:
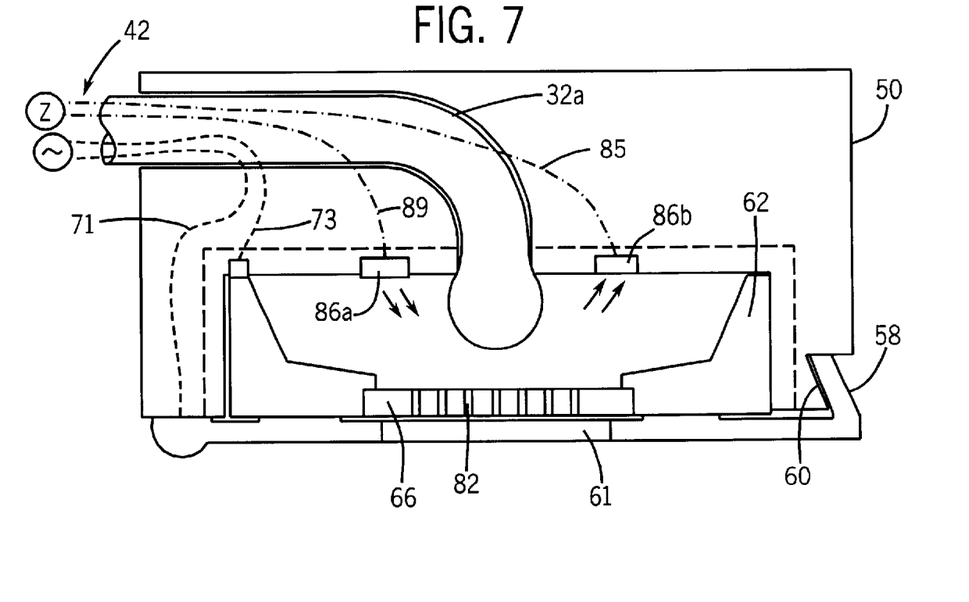
Figure 8A:
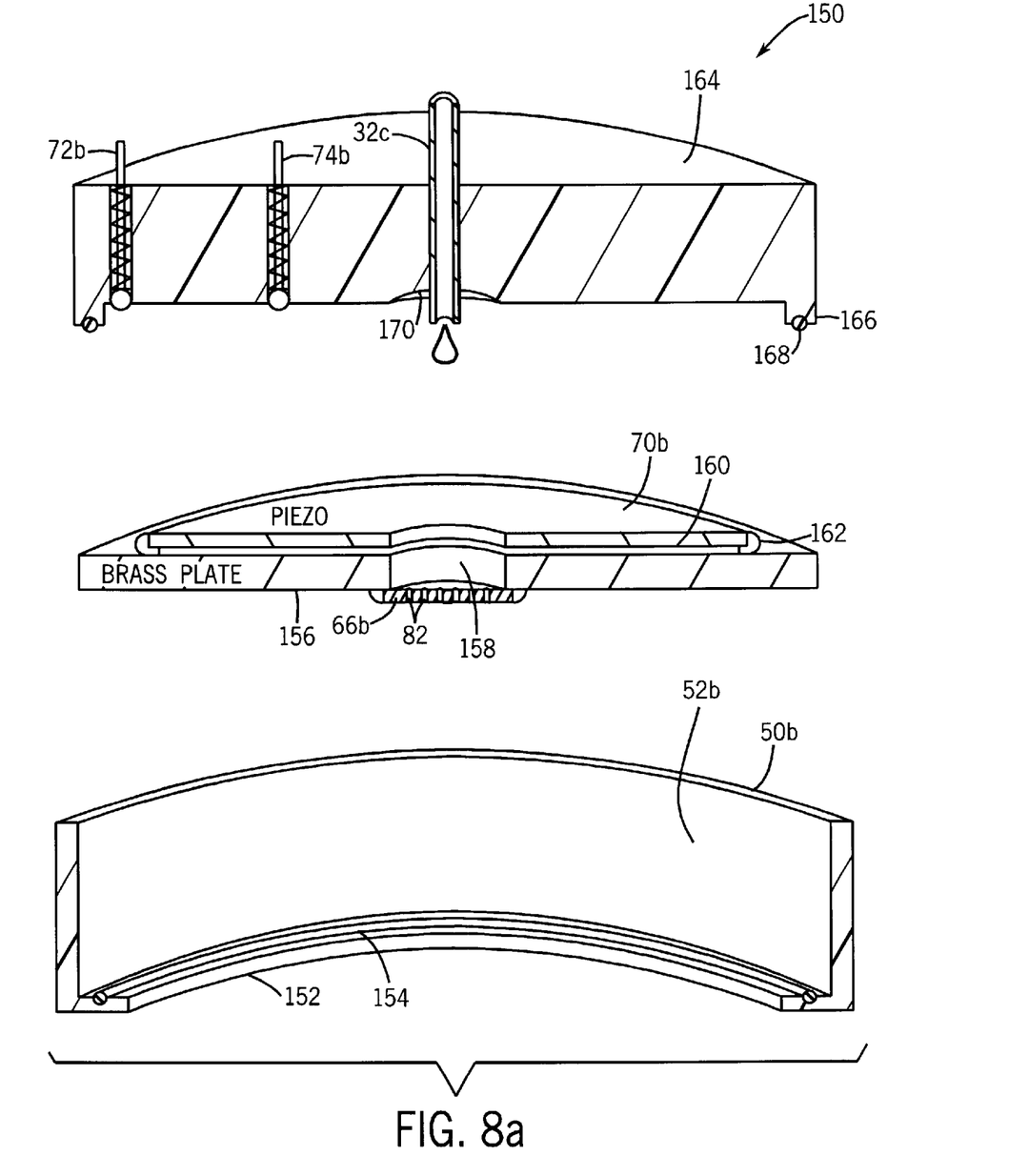
Figure 8B:
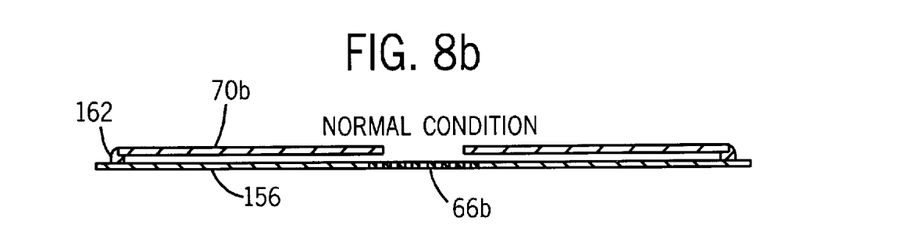
Figure 8C:
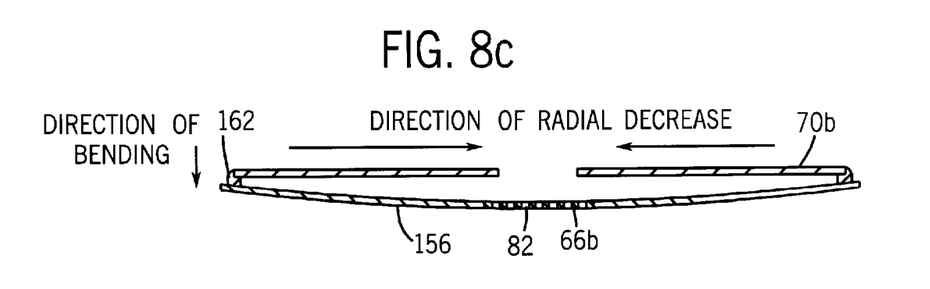

Alternatively, the presence of liquid in volume 80 could be measured by an optical sensor, as shown in FIG. 7, that senses changes in light transmission or reflection caused by the liquid in volume 80. When there is no liquid on mesh plate 66, light from light source 86a is reflected off the mesh plate to detector 86b. The presence of liquid alters the light path.

The proper supply of liquid through the on-demand delivery from transport line 32a, as controlled by electrodes 86, provides the following advantages. If too much liquid were to be delivered to volume 80, liquid would pressurize mesh plate 66 and might leak through mesh plate 66. And, if too much liquid were to be delivered to volume 80, pressure balancing channel 88 could be occluded. This could also result in undesired pressures being applied to mesh plate 66.

If too little liquid is delivered to volume 80, the liquid from transport line 32a may not cover all the holes 82 in mesh plate 66. However, the pressure balancing provided by channel 88 avoids breathing gas flow through the holes in mesh plate 66 in opposition to the liquid being nebulized which might otherwise degrade the operation of nebulizer apparatus 1.

Position insensitivity for nebulizer apparatus 1 is obtained by locating the end of transport line 32a sufficiently close to rear surface 76 of mesh plate 66 that the surface tension in the column of liquid will maintain the column between the end of transport line 32a and rear surface 76 of mesh plate 66. Since liquid is incompressible, should nebulizer apparatus be inverted from the position shown in FIG. 2, the liquid in transport line 32a will support the liquid column in volume 80 so that operation of the nebulizer apparatus is maintained.

In some applications, it may be desirable to heat the liquid to be nebulized, the mesh plate, the mesh plate frame, the housing and/or liquid supply conduit/transport line. For example, the liquid may be heated to body temperature to improve administration of the agent or to prevent discomfort to the patient. Mesh plate 66 or mesh plate frame 62 or housing 50 could be heated for these purposes and to prevent condensation of the liquid or spray on these or other elements. For these purposes, an appropriate heater, for example, a resistor 91, may be employed and controlled through cable 42.

Figure 3:
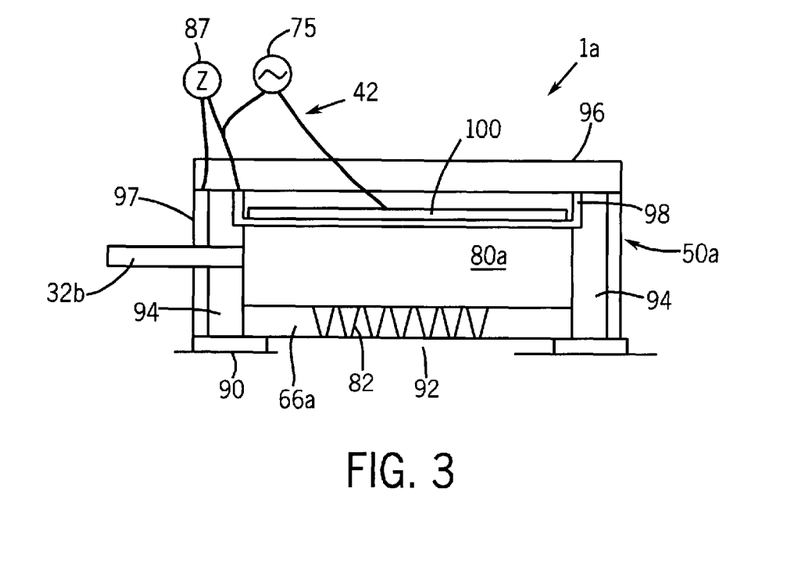

An alternative embodiment of the nebulizer apparatus is shown in FIG. 3. In the nebulizer apparatus 1a of FIG. 3, mesh plate 66a is formed using a conductive material such as nickel, which enables it to function as an electrode for liquid level measurement in volume 80a. Mesh plate 66a rests on annular disc 90 having an opening 92. Annular disc 90 is made of a conductive material that is inert with respect to the liquid to be nebulized and to the breathing gases. Disc 90 forms the base of housing 50a. Housing 50a is completed with a non-conductive tubular sidewall 94 and a non-conductive top plate 96. Top plate 96 may be removable to allow cleaning of the interior components of nebulizer apparatus 1a. Mesh plate 66a is electrically connected to disc 90 and to conductor 97.

Sidewall 94 has an aperture that accommodates transport line 32b. Unlike the embodiment of FIG. 1, the cavity or volume 80a in FIG. 3 is filled with liquid from the side of apparatus 1a, rather than from the top.

Conductive plate 98 is mounted in sidewall 94 as by the upright flange around its perimeter which is directed away from the mesh plate 66a. Plate 98 has several purposes. First, plate 98 mounts ultrasonic vibration generator 100, preferably a piezoelectric element. Ultrasonic vibration generator 100 is affixed to plate 98. Second, plate 98 functions as a liquid level detector in space 80a by serving as an electrode for measurement in conjunction with conductive mesh plate 66a.

In operation, liquid flows into volume 80a from transport line 32b. A control valve, such as valve 40, shown in FIG. 1 is used to control the liquid transported into volume 80a. When the liquid makes contact with mesh plate 66a and with plate 98 serving as sensing electrodes, the impedance measurement between plate 98 and mesh plate 66a changes. The control valve is closed, to be thereafter opened when the liquid level recedes to the point where contact with plate 98 is lost.

Piezoelectric element 100 vibrates the liquid by inducing pressure waves from plate 98. The piezoelectric element is energized by electrical power source 75 in control unit 6 through cable 42. The vibrating liquid is atomized as it passes through holes 82 and discharged into the breathing gases.

Thus, while in nebulizer apparatus of FIG. 1, mesh plate 66 is vibrated by the piezoelectric element, in nebulizer apparatus 1a shown in FIG. 3, the liquid in volume 80a is vibrated by the piezoelectric element.

Figure 4:
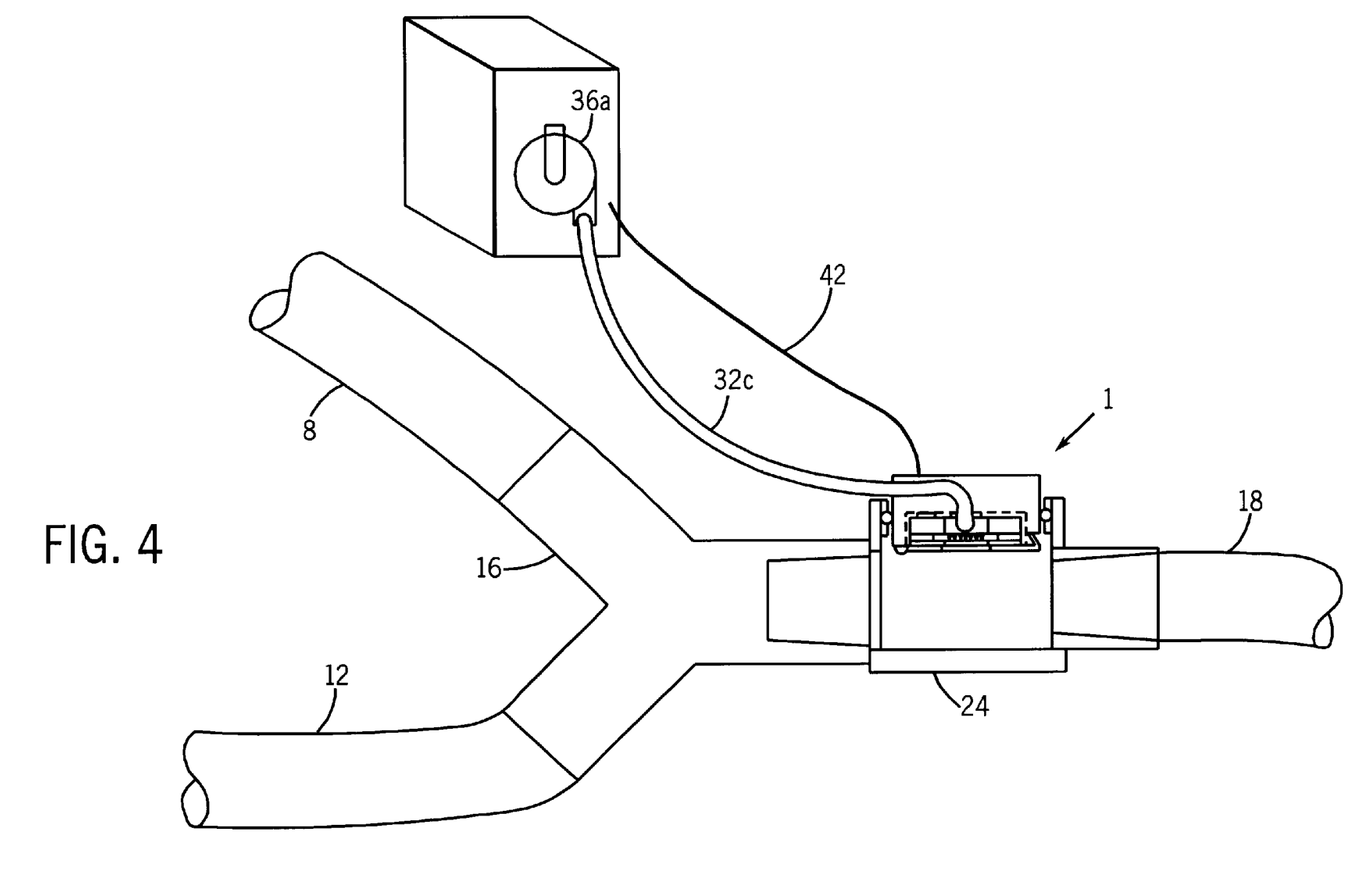

The embodiment of the invention shown in FIG. 4 differs from that shown in FIG. 1 in that pump 36a in control unit 6 supplies liquid directly to transport line 32c from a liquid source (not shown). The control provided by valve 40, shown in FIG. 1, can be achieved by turning pump 36 on and off. Cable 42 obtains electrical signals from the liquid level sensors in nebulizer apparatus 1 for use by control unit 6 in controlling pump 36a. The pump is turned off when the impedance detected by the liquid level sensors indicates that the appropriate amount of liquid has been provided to nebulizer apparatus 1. Use of the pump 36a shown in FIG. 4 has advantages over the pressurizing gas shown in FIG. 1 in that some liquid medications cannot be exposed to the pressurizing gas without deleterious effects.

Figure 5:
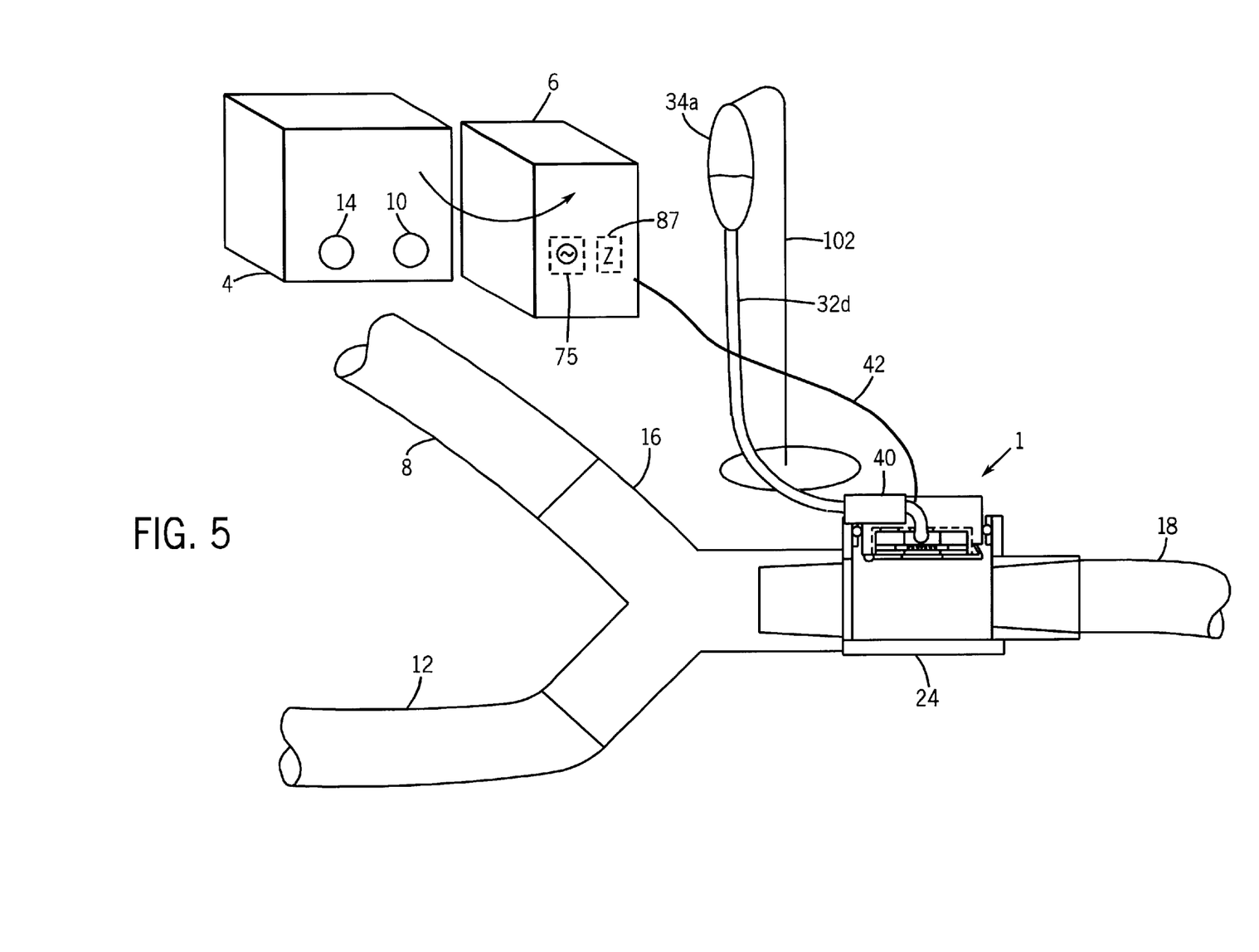
Figure 6A:
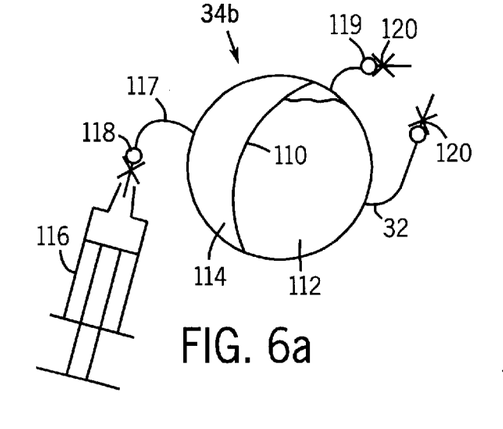
Figure 6B:
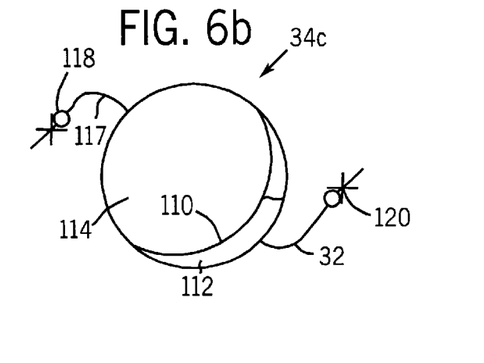
Figure 6C:
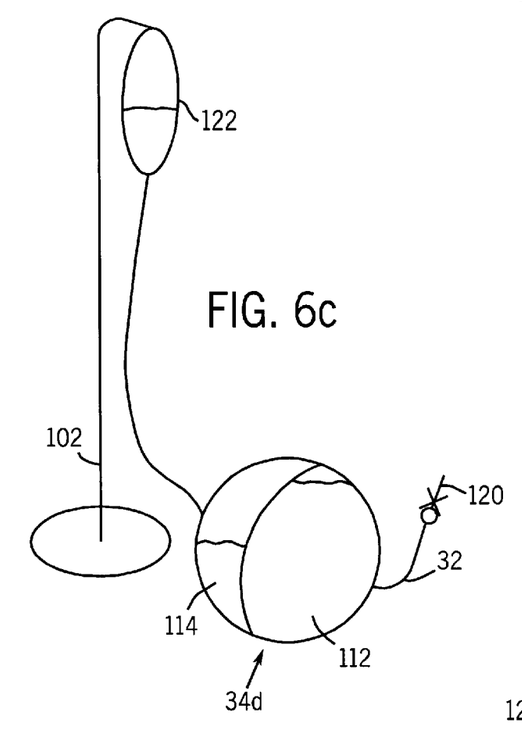
Figure 6D:
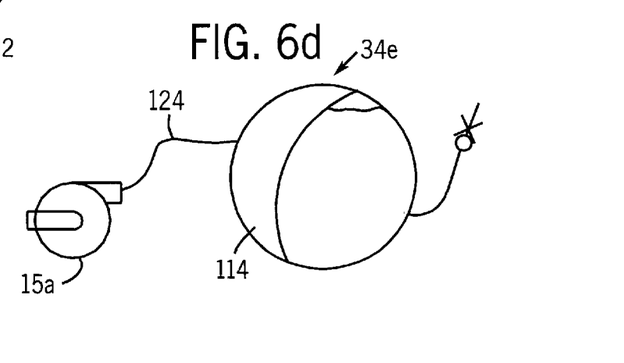

In the embodiment of FIG. 5, the force used to transport the liquid to the nebulizer apparatus is obtained hydrostatically. The liquid source, such as liquid reservoir 34a, can be arranged at an elevated position with respect to nebulizer apparatus 1, 1a to generate a pressure head to supply liquid to the apparatus. Liquid supply 34a may comprise a flexible pouch or bag mounted on stand 102 to create a hydrostatic pressure for causing liquid to flow through transport line 32d when control valve 40 is opened. The arrangement shown in FIG. 5 is especially suitable for nebulizing the large amounts of liquid often required in continuous long term treatment of a subject. The embodiment of FIG. 5 has the advantage in that it will use less energy, and be less noisy, than embodiments using gas or liquid pumps.

FIGS. 6a–d show, in schematic form, various other techniques by which amounts of liquid to be nebulized may be provided to transport line 32. In the alternatives schematically depicted in FIG. 6, the reservoir for the liquid to be nebulized has a flexible wall 110 which keeps the liquid in reservoir chamber 112 separate from a pressurizing agent in chamber 114 which is used to supply the liquid through transport line 32. This avoids contamination of the liquid to be nebulized by the pressurizing agent, and/or insures sterility of the liquid to be nebulized.

In the embodiment of the invention shown in FIG. 6(*a*), syringe 116 is used to pressurize pressure chamber 114 of reservoir 34*b* through line 117 and automatically opening and closing valve 118. Syringe supplies a pressurizing agent, such as a gas, to chamber 114 to pressurize the liquid to be nebulized contained in reservoir chamber 112 of reservoir 34*b*. Syringe 116 may be removed once the pressurization is completed. Liquid reservoir 112 may be loaded with the required dosage of a pharmaceutical agent through conduit 119, sealed with valve 120 or through transport line 32, and pressure chamber 114 pressurized prior to connection of reservoir 34*b* to apparatus 1. Valve 120, which opens when reservoir 34*a* is connected to nebulizing apparatus 1, is provided in conduit 32. FIG. 6*b* shows a reservoir 34*c* which has been filled through transport line 32. The reservoir is shown in a condition in which most of the liquid to be nebulized has been discharged from reservoir chamber 112.

In the embodiment of the invention shown in FIG. 6(*c*), pressure chamber 114 is pressurized by gravitationally supplying a liquid to chamber 114. The liquid is stored in a container 122, elevated above reservoir 34*d* to obtain an adequate head pressure. Container 122 may be kept at the appropriate level using an adjustable stand 102.

In the embodiment of the invention shown in FIG. 6(*d*) the pressure chamber 114 is pressurized by pump 15*a*. The pump may be located, for example, in control unit 6 (shown in FIGS. 1 and 2) and connected to reservoir 34*c* by supply line 124. Pump 15*a* may be either a liquid or gas pump. In operation, pump 15*a* is regulated by control unit 6.

It will be appreciated that the reservoir for the liquid to be nebulized can comprise a pre-filled reservoir containing a desired dosage of a pharmaceutical or other agent to be dispensed by nebulizer apparatus 1 in reservoir chamber 112.

FIGS. 8*a,* 8*b,* and 8*c* show a further embodiment of the nebulizer apparatus of the present invention and in which elements similar or analogous to the embodiments of FIGS. 1 and 3 are indicated with similar reference numerals. Nebulizer apparatus 150 shown in the cross sectional, exploded view of FIG. 8*a* has annular housing 50*b* which mounts the apparatus in adapter 24. Housing 50*b* is formed of plastic or similar material. Lip 152 is formed on the lower edge of housing 50*b* and contains O-ring 154.

Disc-like plate 156, shown with enlarged thickness in FIG. 8*a* and comprised of a conductive material such as brass, is sealed to lip 152 by O-ring 154. Plate 156 contains a central opening 158. The surface of plate 156 which is the lower surface when the nebulizer apparatus is oriented as shown in FIG. 8*a* mounts mesh plate 66*b* containing holes 82. Mesh plate 66*b* may be mounted to plate 156 by gluing, brazing, welding, or other suitable technique.

Piezoelectric element 70*b* is mounted on the upper surface of plate 156. Specifically, piezoelectric element 70*b* is spaced from plate 156 by a small gap 160 and secured to plate 156 about its periphery by a conductive glue, brazing, welding, or other suitable technique, shown as 162 in FIG. 8. Piezoelectric element 70*b* has a central opening corresponding to that of plate 156.

Plug member 164 formed of a non-conductive material, such as plastic, is placed in cavity 52*b* of housing 50*b*. Plug member 164 has depending lip 166 containing O-ring 168. Plug member 164 is placed on top of plate 156 so that the plate is between O-rings 154 and 168.

A central liquid transport line 32*c* extends through plug member 164 to approximately the upper surface of plate 156. A small domed cavity 170 may be formed in the lower surface of plug member 164 to surround transport line 32*c*. Transport line 32*c* may be formed of a conductive material to allow its use in impedance measurement of the presence of liquid in nebulizer apparatus 150.

An electric power terminal 74*b* extends through plug member 164. The lower end of terminal 74*b,* which terminal may be in the form of a spring loaded pin, contacts piezoelectric element 70*b*. The upper end of terminal 74*b* is connected to cable 42. A second electrical power terminal 72*b* also extends through plug member 164. The lower end of terminal 72*b* contacts conductive plate 156. The upper end of terminal 72*b* is connected to cable 42. Terminal 72*b* may be electrically grounded for purposes of applying a voltage to piezoelectric element 70*b* in conjunction with terminal 74*b,* as well as for impedance measurement in conjunction with conductive liquid transport line 32*c*.

In operation, alternating voltage is supplied from power source 75 through cable 42 and terminals 72*b* and 74*b* to piezoelectric element 70*b* which vibrates the element. The vibrations cause the element to contract from the normal condition, shown in FIG. 8*b* to a radially decreased condition shown in FIG. 8*c* and return to the normal condition. Due to the joinder of piezoelectric element 70*b* to plate 156 about the periphery of the element, the radial size reduction of piezoelectric element 70*b* causes plate 156 to bow, as shown in FIG. 8*c,* and then return to the flat condition, shown in FIG. 8*b,* when piezoelectric element 70*b* returns to the normal state. The action of plate 156 shown in FIGS. 8*b* and 8*c* discharges nebulized liquid from holes 82 in mesh plate 66*b*.

It is recognized that other equivalents, alternatives, and modifications aside from those expressly stated, are possible and within the scope of the appended claims.

What is claimed is:

1. A nebulizer apparatus for atomizing a liquid into an aerosol of fine droplets, said nebulizer apparatus comprising:

a housing having a cavity with an opening;

a thin mesh plate positioned across the opening of the cavity, said mesh plate having an exposed front surface and a rear surface facing into said cavity, said mesh plate having holes extending through said mesh plate from the front surface to the rear surface;

a liquid transport line opening into said cavity for supplying a volume of liquid to the rear surface of said mesh plate;

a vibration generator energizable to establish vibrations in one of the mesh plate or liquid to cause the liquid to pass through the holes in the mesh plate and to be discharged from the front surface of the plate as an aerosol of fine droplets;

a sensor located in said cavity, said sensor measuring the extent of a physical dimension of the volume of liquid supplied to the rear surface of said mesh plate; and means for controlling a supply of liquid from said liquid transport line to said cavity, responsive to said sensor, to maintain a desired volume of liquid on the rear surface of said mesh plate.

2. The apparatus of claim 1 wherein the holes have diameters and wherein the diameters of the holes are larger at the rear surface of the mesh plate and decrease along extensions of the holes through the mesh plate to smaller diameters at the front surface of the plate.

3. The apparatus of claim 1 wherein said holes are straight holes.

4. The apparatus of claim 1 wherein the vibration generator comprises a piezoelectric element.

5. The apparatus of claim 4 wherein said vibrator means is coupled to said mesh plate to vibrate the plate.

6. The apparatus of claim 5 wherein said holes are in a central portion of said mesh plate and wherein said vibration generator is peripherally joined to said mesh plate to surround said central portion, energization of said vibration generator causing a bowing action in said mesh plate.

7. The apparatus of claim 4 wherein said vibration generator contacts the liquid to induce pressure waves in the liquid.

8. The apparatus of claim 1 wherein the liquid transport line is further defined as supplying liquid to form a column of liquid on the rear surface of said mesh plate.

9. The apparatus of claim 1 wherein said sensor comprises spaced elements establishing an impedance therebetween and wherein said sensor measures the extent of a physical dimension of the volume of liquid supplied to the rear surface of said mesh plate by changes in impedance between said spaced elements produced by the liquid.

10. The apparatus of claim 9 wherein said spaced elements comprise a pair of spaced electrodes in said cavity.

11. The apparatus of claim 10 wherein said liquid transport line has an opening in said cavity on a surface opposite said rear surface of said mesh plate and wherein said electrodes are adjacent the opening of said liquid transport line.

12. The apparatus of claim 9 wherein said mesh plate forms one of said spaced elements.

13. The apparatus of claim 12 wherein a portion of said liquid transport line adjacent the opening of said liquid transport line forms the other of said spaced elements.

14. The apparatus of claim 9 wherein a portion of said liquid transport line adjacent the opening of said liquid transport line forms one of said spaced elements.

15. The apparatus of claim 1 wherein said sensor comprises an optical sensor.

16. The apparatus of claim 1 including means for equalizing pressure at the rear surface of the mesh plate and pressure at the front surface of the mesh plate.

17. The apparatus of claim 16 further including a pressure balance channel in said housing between said front and rear surfaces of said mesh plate, whereby the pressures at the front surface and the rear surface are equalized.

18. The apparatus of claim 1 wherein the means for controlling a supply of liquid comprises a valve in said liquid transport line.

19. The apparatus of claim 18 further including means for pressurizing the liquid in said liquid transport line.

20. The apparatus of claim 19 wherein the liquid is contained in a reservoir connected to the liquid transport line and wherein said means for pressurizing is a gas pump for pressurizing the reservoir.

21. The apparatus of claim 19 wherein the liquid is contained in a reservoir elevated with respect to said nebulizer apparatus for pressurizing the liquid with a hydrostatic head.

22. The apparatus of claim 1 wherein the means for controlling a supply of liquid comprises a pump coupled to said liquid transport line.

23. The apparatus of claim 1 further including a reservoir for storage of the liquid prior to atomization, wherein the reservoir is connected to said liquid transport line for delivery of the liquid to the rear surface of the mesh plate.

24. The apparatus of claim 23 wherein said reservoir comprises a two-part container having a deformable liquid reservoir within a part of the container which can be pressurized for pressurizing said liquid reservoir.

25. The apparatus of claim 24 further including a gas pump for pressurizing the part of the container.

26. The apparatus of claim 24 further including an elevated liquid reservoir connected to said part of said container to provide a hydrostatic force for pressurizing said liquid reservoir.

27. The apparatus of claim 1 further defined as a nebulizer apparatus for delivering an aerosol to the breathing gas of a subject passing in a breathing circuit, said apparatus including an adapter for coupling said housing to the breathing circuit.

28. The apparatus of claim 27 including a reservoir connected to said liquid transport line for storing the liquid to be atomized.

29. The apparatus of claim 1 further including a heater.

* * * * *